United States Patent
Cotter (10) Patent No.: US 7,576,323 B2
(45) Date of Patent: Aug. 18, 2009

(54) POINT-OF-CARE MASS SPECTROMETER SYSTEM

(75) Inventor: Robert James Cotter, Baltimore, MD (US)

(73) Assignee: Johns Hopkins University, Baltimore, MD (US)

( * ) Notice: Subject to any disclaimer, the term of this patent is extended or adjusted under 35 U.S.C. 154(b) by 325 days.

(21) Appl. No.: 11/663,844

(22) PCT Filed: Sep. 27, 2005

(86) PCT No.: PCT/US2005/034868

§ 371 (c)(1),
(2), (4) Date: Mar. 27, 2007

(87) PCT Pub. No.: WO2006/037059

PCT Pub. Date: Apr. 6, 2006

(65) Prior Publication Data

US 2008/0258054 A1    Oct. 23, 2008

Related U.S. Application Data

(60) Provisional application No. 60/613,269, filed on Sep. 27, 2004.

(51) Int. Cl.
*H01J 49/00* (2006.01)
*C07G 11/00* (2006.01)
*A61K 38/00* (2006.01)

(52) U.S. Cl. ............ 250/288; 250/281; 250/282; 435/69.7; 435/239; 536/16.9; 536/127; 530/300

(58) Field of Classification Search ............... 250/281, 250/282, 288; 435/68.1, 69.1, 69.7, 235.1, 435/239; 536/16.9, 23.5, 23.6, 23.7, 127; 530/300–303, 322, 323, 332, 333
See application file for complete search history.

(56) References Cited

U.S. PATENT DOCUMENTS 5,101,105 A    3/1992    Fenselau et al.

(Continued)

FOREIGN PATENT DOCUMENTS

WO    WO 03/086589    10/2003

(Continued)

OTHER PUBLICATIONS

Hunt, D.F., et al., "Characterization of Peptides Bound to the Class I MHC Molecule HLA-A2.1 by Mass Spectrometry," *Science* 255, pp. 1261-1263 (1992).

(Continued)

*Primary Examiner*—Bernard E Souw
(74) *Attorney, Agent, or Firm*—Venable LLP; Henry J. Daley (57) ABSTRACT

A point-of-care mass spectrometer system has a sampling system, an ionization component structured to receive a sample for analysis from the sampling system, a mass analyzer structured to receive a source of ions for analysis from the ionization component, and a detector structured to detect ions from the mass analyzer and to generate an output signal. The sampling system selects a subset of peptides from a sample by immunopurification of multiple histocompatability complexes and concentrates the subset of peptides to provide the sample to the ionization component.

27 Claims, 4 Drawing Sheets

U.S. PATENT DOCUMENTS

| | | | |
|---|---|---|---|
| 5,202,563 | A | 4/1993 | Cotter et al. |
| 5,399,857 | A | 3/1995 | Doroshenko et al. |
| 5,464,985 | A | 11/1995 | Cornish et al. |
| 5,572,025 | A | 11/1996 | Cotter et al. |
| 5,696,376 | A | 12/1997 | Doroshenko et al. |
| 5,770,201 | A | 6/1998 | Goulmy et al. |
| 5,814,813 | A | 9/1998 | Cotter et al. |
| 5,830,641 | A | 11/1998 | Montagnier et al. |
| 5,844,075 | A | 12/1998 | Kawakami et al. |
| 5,874,560 | A | 2/1999 | Kawakami et al. |
| 5,994,523 | A | 11/1999 | Kawakami et al. |
| 6,139,734 | A | 10/2000 | Settlage et al. |
| 6,270,778 | B1 | 8/2001 | Kawakami et al. |
| 6,315,905 | B1 | 11/2001 | Settlage et al. |
| 6,365,892 | B1 | 4/2002 | Cotter et al. |
| 6,498,039 | B2 | 12/2002 | Nelson |
| 6,518,568 | B1 | 2/2003 | Kovtoun et al. |
| 6,521,598 | B1 | 2/2003 | Goulmy et al. |
| 6,537,560 | B1 | 3/2003 | Kawakami et al. |
| 6,558,671 | B1 | 5/2003 | Slingluff et al. |
| 6,558,902 | B1 | 5/2003 | Hillenkamp |
| 6,660,276 | B1 | 12/2003 | Slingluff et al. |
| 6,756,586 | B2 | 6/2004 | Caprioli |
| 6,908,740 | B2 | 6/2005 | Vandekerckhove et al. |
| 7,335,486 | B2 * | 2/2008 | Wagner et al. ............. 435/68.1 |
| 7,372,021 | B2 * | 5/2008 | Cotter et al. ................ 250/287 |
| 7,488,791 | B2 * | 2/2009 | Maillere et al. ............. 530/300 |
| 7,498,148 | B2 * | 3/2009 | Wagner et al. ............. 435/68.1 |
| 2001/0036669 | A1 * | 11/2001 | Jedrzejewski et al. ......... 436/94 |
| 2002/0037532 | A1 * | 3/2002 | Regnier et al. ............... 435/7.1 |
| 2003/0073145 | A1 | 4/2003 | Caprioli |
| 2003/0119063 | A1 | 6/2003 | Pham |
| 2003/0153007 | A1 | 8/2003 | Chen |
| 2003/0175250 | A1 * | 9/2003 | Jager et al. ................. 424/93.7 |
| 2004/0005633 | A1 | 1/2004 | Vandekerckhove et al. |
| 2004/0209808 | A1 * | 10/2004 | Kornacker ................... 514/12 |
| 2004/0214783 | A1 | 10/2004 | Terman |
| 2004/0224338 | A1 | 11/2004 | Chicz et al. |
| 2004/0235186 | A1 * | 11/2004 | Gygi et al. .................. 436/166 |
| 2004/0259164 | A1 * | 12/2004 | Gygi et al. ................... 435/7.1 |
| 2005/0029444 | A1 | 2/2005 | Caprioli |
| 2005/0069916 | A1 * | 3/2005 | Chait et al. ..................... 435/6 |
| 2005/0158745 | A1 | 7/2005 | Ye |
| 2005/0196823 | A1 | 9/2005 | Vandekerckhove et al. |
| 2005/0202485 | A1 | 9/2005 | Ye |
| 2006/0019339 | A1 * | 1/2006 | Lauth et al. ................. 435/69.1 |
| 2006/0134744 | A1 * | 6/2006 | Hildebrand et al. ......... 435/69.1 |
| 2007/0029474 | A1 * | 2/2007 | Cotter et al. ................ 250/287 |
| 2007/0034794 | A1 * | 2/2007 | Cotter et al. ................ 250/287 |
| 2008/0258054 | A1 * | 10/2008 | Cotter ......................... 250/288 |

FOREIGN PATENT DOCUMENTS

| | | |
|---|---|---|
| WO | WO 03/103008 | 12/2003 |
| WO | WO 03/107387 | 12/2003 |
| WO | WO 2004/013602 | 2/2004 |
| WO | WO 2004/040612 | 5/2004 |

OTHER PUBLICATIONS

Henderson, R.A., et al., "HLA-A2.1-Associated Peptides from a Mutant Cell Line: a Second Pathway of Antigen Presentation," *Science* 255, pp. 1264-1266 (1992).

Hunt, D.F., et al., "Peptides Presented to the Immune System by the Murine Class II Major Histocompatability Complex Molecule I-Ad," *Science* 256, pp. 1817-1820 (1992).

Henderson, R.A., et al., "Direct Identification of an Endogenous Peptide Recognized by Multiple HLA-A2.1-Specific Cytotoxic T Cells," Proc. Natl. Acad. Sci. USA 90, pp. 10275-10279 (1993).

Woods, A.S., et al., "Simplified High-Sensitivity Sequencing of a Major Histocompatability Complex Class I-Associated Immunoreactive Peptide Using Matrix-Assisted Laser Desorption/Ionization Mass Spectrometry," *Anal. Biochem.* 226, pp. 15-25 (1995).

Huang, A.Y.C., et al., "The Immunodominant Major Histocompatability Complex Class I-Restricted Antigen of a Murine Colon Tumor Derives from an Endogenous Retroviral Gene Product," *Pro. Natl. Acad. Sci. USA* 93, pp. 9730-9735 (1996).

Aldrich, C.J., et al., "Identification of a Tap-Dependent Leader Peptide Recognized by Alloreactive T Cells Specific for a Class Ib Antigen," *Cell* 79, pp. 649-658 (1994).

DeCloux, A., et al., "Dominance of a Single Peptide Bound to the Class $I_B$ Molecule, Qa-$1^{b1}$," *J. Immunol.* 158, pp. 2183-2191 (1997).

Lo, W.-F., et al. "Molecular Mimicry Mediated by MHC Class $I_B$ Molecules Following Infection with Gram-Negative Pathogens," *Nature Medicine* 6, pp. 215-218 (2000).

Prieto, M.C., et al., "Miniaturized Linear Time-of-Flight Mass Spectrometer with Pulsed Extraction," *J. Mass Spectrom.* 37, pp. 1158-1162 (2002).

English, R.D., et al., "*Bacillus* Spore Identification Using Proteolytic Mapping and a Miniaturized MALDI TOF Mass Spectrometer," *Anal. Chem.* 75, pp. 6886-6893 (2003).

Cornish, T.J., et al., "High Order Kinetic Energy Focusing in Endcap Reflectron Time-of-Flight Mass Spectrometer," *Anal. Chem.* 69, pp. 4615-4618 (1997).

Cotter, R.J., et al., "Miniaturized Time-of-Flight Mass Spectrometer for Peptide and Oligonucleotide Analysis," *J. Mass Spectrom.* 34, pp. 1368-1372 (1999).

Fancher, C.A., et al., "Improving the Sensitivity of the Endcap Reflectron Time-of-Flight Mass Spectrometer," *J. Am. Chem. Soc.* 35, pp. 157-162 (2000).

Berkout, V.D., et al., "Miniaturized EI/Q/oa TOF Mass Spectrometer" *J. Am. Soc. Mass Spectrom.* 12, pp. 641-647 (2001).

Cotter, R.J., et al., "Tandem Time-of-Flight Mass Spectrometry with a Curved Field Reflectron," *Anal. Chem.* 76, pp. 1976-1981 (2004).

Written Opinion of the International Search Authority, (Dec. 1, 2006).

US 5,809,475, 09/1998, Yee et al. (withdrawn)

* cited by examiner

POINT-OF-CARE MASS SPECTROMETER SYSTEM

CROSS-REFERENCE OF RELATED APPLICATION

This application claims priority to International Application No. PCT/US2005/034868, filed Sep. 27, 2005 and U.S. Application No. 60/613,269, filed Sep. 27, 2004, the entire contents of which are hereby incorporated by reference.

The U.S. Government has a paid-up license in this invention and the right in limited circumstances to require the patent owner to license others on reasonable terms as provided for by the terms of NIH Grant No. GM54882 for "Sequencing of Class 1 MHC Peptides by Mass Spectrometry."

BACKGROUND

1. Field of Invention

The current invention relates to clinical diagnostic systems and methods, and more particularly to point-of-care mass spectrometer systems and methods.

2. Discussion of Related Art

Figure 1:
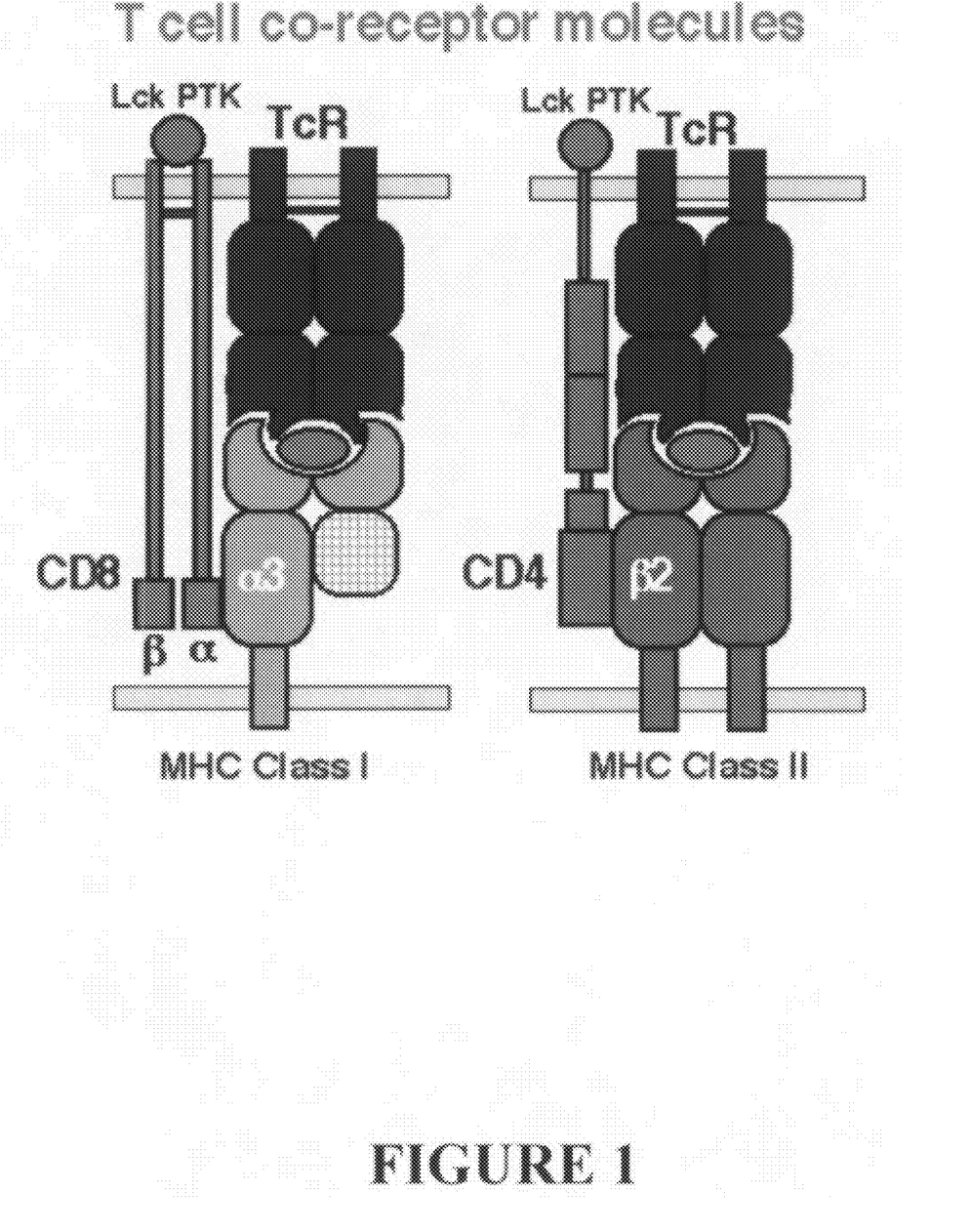
FIG. 1 is a schematic representation of MHC class I and class II complexes and their TcR receptors on killer (CTL) T cells and helper T cells, respectively.

Proteins synthesized in the nucleus of cells are degraded into small peptides by proteasomes as part of the natural turnover process. In the class I system these (generally nine amino acid) peptides are passed into the endoplasmic reticulum via the TAP transporter channel and combined with the multiple histocompatability (MHC) molecule, forming a complex that is transported to the cell surface and displayed to the immune system. Both the MHC and antigen are recognized by killer T cells or cytotoxic T lymphocytes (CTLs) and is known as restricted recognition (see FIG. 1). Failure to recognize either the MHC molecule or the antigen as self molecules produces a complex immunological response that results in cell lysis and cell death. Non-self MHC molecules may occur as a result of the presence of non-self cells (as is the case in organ or tissue transplantation) and, in essence, results in rejection. Non-self peptides are those that are synthesized in the nucleus of the cell as a result of viral or retroviral infection, or from altered cells, such as those produced in cancer. In this case the immune response is to rid the body of infected or altered cells. In some rarer cases, CTLs react to the presence of self peptides, producing an autoimmune disease. Beginning with the pioneering work of Hunt et al. (see Hunt, D. F.; Henderson, R. A.; Shabanowitz, J.; Sakaguchi, K.; Michel, H.; Sevilir, N.; Cox, A. L.; Appella, E.; Englehard, V. H., *Characterization of Peptides Bound to the Class I MHC Molecule HLA-A2.1 by Mass Spectrometry*, Science 255 (1992) 1261-1263; Henderson, R. A.; Michel, H.; Sakaguchi, K.; Shabanowitz, J.; Appella, E.; Hunt, D. F.; Englehard, V. H., *HLA-A2.1-Associated Peptides from a Mutant Cell Line: a Second Pathway of Antigen Presentation*, Science 255 (1992) 1264-1266; Hunt, D. F.; Michel, H.; Dickenson, T. A.; Shabanowitz, J.; Cox, A. L.; Sakaguchi, K.; Appella, E. Grey, H. M.; Settee, A., *Peptides Presented to the Immune System by the Murine Class II Major Histocompatability Complex Molecule I-Ad*, Science 256 (1992) 1817-1820; Henderson, R. A.; Cox, A. L.; Sakaguchi, K.; Appella, E.; Shabanaowitz, J.; Hunt, D. F.; Engelhard, V. H., *Direct Identification of an Endogenous Peptide Recognized by Multiple HLA-A2.1-Specific Cytotoxic T Cells, Proc.* Natl. Acad. Sci. USA 90 (1993) 10275-10279, the entire contents of which are incorporated herein by reference), mass spectrometry has been used for a number of years for the structural characterization or amino acid sequencing of both class I (viral) and class II (bacterial) antigens.

Most of these research studies have utilized electrospray ionization (ESI) because of the ability to directly couple high performance liquid chromatography (HPLC) fractionation with the mass spectrometer. However, there remains a need for mass spectrometer systems and methods that are portable and/or can be used at the point of care.

Patents related to MHC class I antigens include U.S. Pat. No. 6,660,276; U.S. Pat. No. 6,558,671; U.S. Pat. No. 6,521,598; U.S. Pat. No. 6,315,905; U.S. Pat. No. 6,139,734; U.S. Pat. No. 5,770,201; U.S. Pat. No. 6,537,560; U.S. Pat. No. 6,270,778; U.S. Pat. No. 5,994,523; U.S. Pat. No. 5,874,560; U.S. Pat. No. 5,844,075; U.S. Pat. No. 5,809,475; and U.S. Pat. No. 5,830,641 each of which is incorporated herein by reference.

Patents related to mass spectrometers include U.S. Pat. No. 5,101,105, Neutralization/chemical reionization tandem mass spectrometry method and apparatus therefore, Fenselau, C.; Cotter, R. J., Mar. 31, 1992; U.S. Pat. No. 5,202,563, Tandem time-of-flight mass spectrometer, Cotter, R. J.; Cornish, T. J., Apr. 13, 1993; U.S. Pat. No. 5,399,857, Method and apparatus for trapping ions by increasing trapping voltage during ion introduction, Doroshenko, V. M; Cotter, R. J., Mar. 21, 1995; U.S. Pat. No. 5,464,985, Non-linear reflectron, Cornish, T. J.; Cotter, R. J., Nov. 7, 1995; U.S. Pat. No. 5,572,025, Method and apparatus for scanning an ion trap mass spectrometer in the resonance ejection mode, Cotter, R. J.; Doroshenko, V. M., Nov. 5, 1996; U.S. Pat. No. 5,696,376, Method and apparatus for isolating ions in an ion trap with increased resolving power, Doroshenko, V. M.; Cotter, R. J., Dec. 9, 1997; U.S. Pat. No. 5,814,813, Endcap reflectron for a time-of-flight mass spectrometer and method of using the same, Cotter, R. J.; Cornish, T. J., Sep. 29, 1998; U.S. Pat. No. 6,365,892, Method and apparatus for correction of initial ion velocity in a reflectron time-of-flight mass spectrometer, Cotter, R. J.; Doroshenko, V. M., Apr. 2, 2002, U.S. Pat. No. 6,518,568, Method and apparatus of mass-correlated pulsed extraction for a time-of-flight mass spectrometer, Kovtoun, V.; Cotter, R. J., Feb. 11, 2003, DM4042 (WO 2004/040612) Combined chemical/biological agent mass spectrometer detector, Cotter, R. J; DM4046 (WO 03/086589) Miniaturized sample-scanning mass spectrometer, Cotter, R. J; DM4077 (WO 03/107387) Non-linear time-of-flight mass spectrometer, Cotter, R. J.; Gardner, B. D; DM4080 (WO 03/103008) Time-of-flight mass spectrometer combining fields non-linear in time and space, Cotter, R. J.; Gardner, B. D.; Holland, J. D; DM4195, Tandem time-of-flight mass spectrometry, Cotter, R. J.; Iltchenko, S.; Gardner, B.; English, R. D.; DM4112 (WO 2004/013602); Combined Chemical/Biological Agent Detection by Mass Spectrometry, Bryden, W.; Cotter, R. J.; Eicelberger, S. each of which is incorporated herein by reference.

SUMMARY

A point-of-care mass spectrometer system has a sampling system; an ionization component structured to receive a sample for analysis from the sampling system; a mass analyzer structured to receive a source of ions for analysis from the ionization component, and a detector structured to detect ions from the mass analyzer and to generate an output signal. The sampling system selects a subset of peptides from a sample by immunopurification of multiple histocompatability complexes and concentrates the subset of peptides to provide the sample to the ionization component.

A clinical diagnostic method includes extracting a subset of peptides from a sample from a subject by immunopurification, ionizing at least a portion of the subset of peptides to provide an ionized sample of peptides, mass analyzing the ionized sample peptides to provide a mass analyzed sample of peptides, detecting the mass analyzed sample of peptides to obtain a measured mass spectrum, and comparing the measured mass spectrum to a reference mass spectrum.

Further objectives and advantages will become apparent from a consideration of the description, drawings, and examples.

BRIEF DESCRIPTION OF THE DRAWINGS

The invention is better understood by reading the following detailed description with reference to the accompanying figures in which.

DETAILED DESCRIPTION

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose. Each reference cited here is incorporated by reference as if each were individually incorporated by reference.

The current inventor and collaborators have pioneered the use of matrix-assisted laser desorption/ionization (MALDI) analysis of antigen mixtures fractionated off-line in a series of HPLC or other chromatographic separations. (See Woods, A. S.; Huang, A. Y. C.; Cotter, R. J.; Pasternack, G. R.; Pardoll, D. M.; Jaffee, E. M., *Simplified High-Sensitivity Sequencing of a Major Histocompatability Complex Class I-Associated Immunoreactive Peptide Using Matrix-Assisted Laser Desorption/Ionization Mass Spectrometry*, Anal. Biochem. 226 (1995) 15-25; Huang, A. Y. C.; Gulden, P. H.; Woods, A. S.; Thomas, M. C.; Tong, C. D.; Wang, W.; Engelhard, V. H.; Pasternack, G.; Cotter, R.; Hunt, D.; Pardoll, D. M.; Jaffee, E. M., *The Immunodominant Major Histocompatability Complex Class I-Restricted Antigen of a Murine Colon Tumor Derives from an Endogenous Retroviral Gene Product*, Proc. Natl. Acad. Sci. USA 93 (1996) 9730-9735; the entire contents of which are incorporated herein by reference.)

While the Hunt group has initially concentrated on the characterization of human leukocyte antigens (HLAs), the current inventor and collaborators have characterized antigens from a specialized class IB antigen from mouse, including a mimic of mammalian heat shock protein (HSP) resulting from infection with Salmonella. (See, Aldrich, C. J.; DeCloux, A.; Woods, A. S.; Cotter, R. J.; Soloski, M. J.; Forman, J., *Identification of a Tap-Dependent Leader Peptide Recognized by Alloreactive T Cells Specific for a Class Ib Antigen*, Cell 79 (1994) 649-658; DeCloux, A.; Woods, A. S.; Cotter, R. J.; Soloski, M. J. and Forman, J., *Dominance of a Single Peptide Bound to the Class $I_B$ Molecule, Qa-$1^{b1}$*, J. Immunol. 158 (1997) 2183-2191; the entire contents of which are incorporated herein by reference.)

Structural characterization (i.e.: amino acid sequencing) of MHC class I antigens and validation of their biological role requires a number of complex experimental procedures that includes (a) initial isolation of MHC/peptide complexes by size exclusion chromatography, (b) purification or immunoprecipitation of complexes using antibodies to MHC, in particular to the β-microglobulin chain, (c) HPLC purification to separate the individual peptides, (d) CTL assays of each fraction to determine bioactive peptides eluting from the HPLC, (e) development of the antigen specific CTL assays, (f) high performance mass spectrometry to determine molecular weights, (g) MS/MS analysis to determine amino acid sequences, and (h) chemical synthesis of the antigen and demonstration of its bioactivity.

Figure 2:
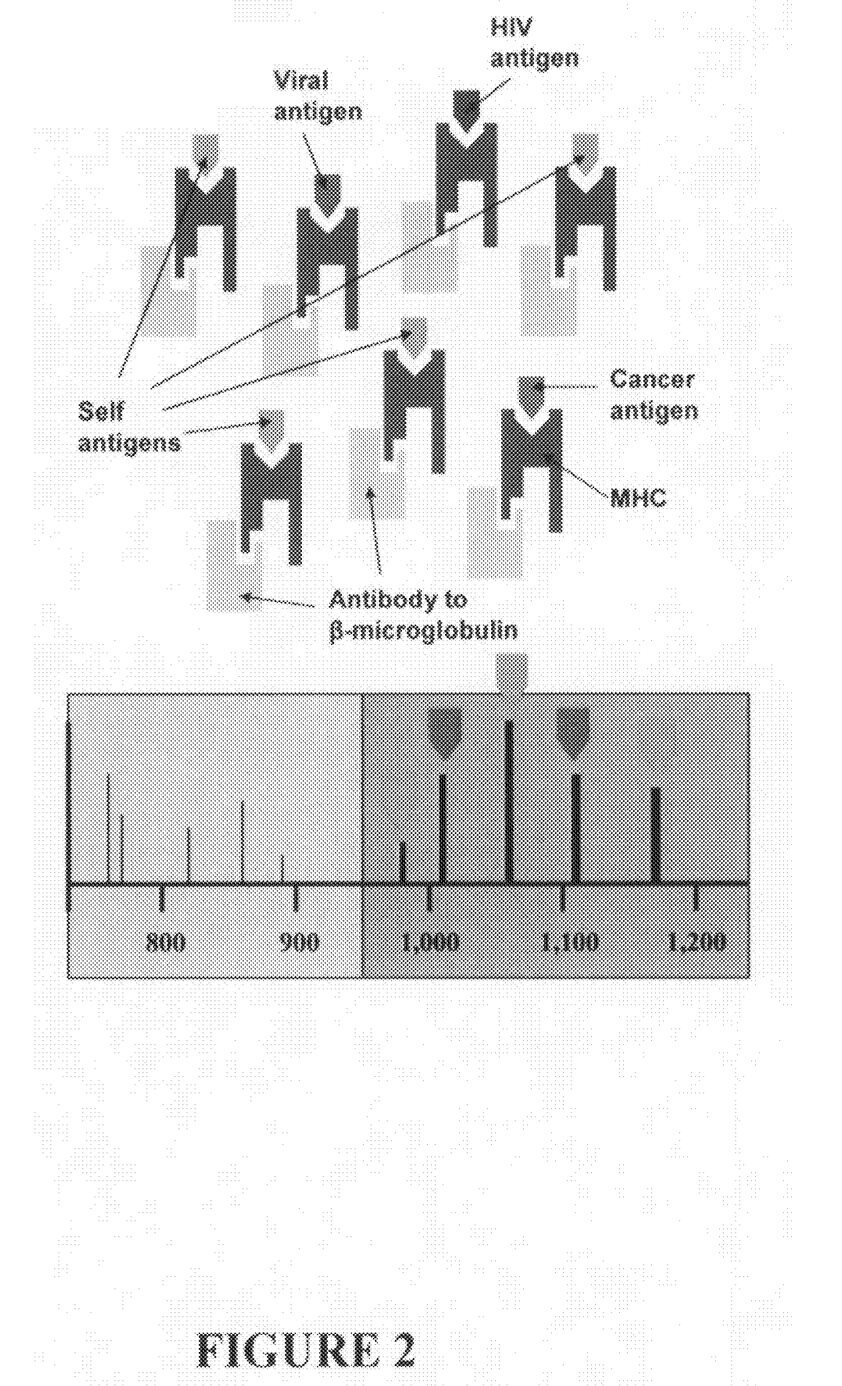
FIG. 2 is a schematic representation of immunoprecipitation of MHC-peptide complexes and mass spectrum of the bound peptides following elution into the mass spectrometer.

In a diagnostics mode which is envisioned here, characterization of individual, purified peptides and demonstration of bioactivity is not required. This reduces the performance requirements for both chromatographic separations and mass spectrometric analyses and forms a basis for an embodiment of a point-of-care mass spectrometry system. In this approach, the mass spectrometer records a molecular ion mass spectrum of the entire set or a partially fractionated set of antigens displayed by the class I MHC molecules. The set of peptides presented to the mass spectrometer are derived from blood or plasma by extraction of the MHC-peptide complexes, immunoprecipitation, elution of the bound peptides, and/or partial fractionation. These steps are carried out in an integrated front-end sampling system that is inserted into the mass spectrometer in an embodiment of this invention. In an embodiment, elution and concentration of the sample on a small spot works well. As shown in FIG. 2, one specific approach is to utilize an antibody to β-microglobulin, immobilized on a sample collection surface, to extract MHC complexes containing self, viral, HIV and/or cancer antigens as a class. The bound peptides are eluted before or after insertion into the mass spectrometer, concentrated and mass analyzed to produce a series of molecular ion peaks that correspond to both self and foreign antigens. While these are not characterized directly, masses may be correlated with masses of currently known antigens, with antigens commonly observed for this patient, or with those associated statistically with disease states as determined from a broader patient population.

This approach can be thought of in analogy to the proteomics approaches used for biomarker discovery from complex protein mixtures obtained from blood, plasma, urine, breath, etc. in which the biomarkers that will be used for diagnoses are identified by statistical association with particular disease states. Because the human proteome is a very complex array of thousands of proteins which range widely in mass over many orders of magnitude in abundance, it has become common to isolate smaller subsets of the proteome (subproteomes) prior to HPLC fraction, or 2D gel electrophoresis. While the mixture of class I antigens does also represent a complex mixture, it is not nearly as daunting, since the peptide masses lie within a small mass range (for example 700 to 1600 Daltons) and the MHC molecule provides the means to obtain a limited set of peptides (in essence a subpeptidome). The observation of hundreds to thousands of different peptides over this small mass range does indeed provide serious limitations for de novo characterization, as many of these will necessarily have the same mass. However, correlation of the mass display with specific disease states should be achieveable. For example, a change in intensity of a peak may be indicative of a condition even if the peak represents more than one kind of peptide (biomarker). Or, changes in intensities may occur for several different peaks and the entire pattern may be correlated. Alternatively, point-of-care instruments designed with higher mass resolution or MS/MS capability may be used to distinguish these isomass ions.

An aspect of the current invention is an apparatus and method for clinical diagnostics using mass spectrometry technology that can be brought to the point-of-care to provide a single broad-based assessment of viral infection, HIV and/or cancer. In an embodiment of this invention, one records a survey mass spectrum of an unfractionated or partially fractionated antigen display of class I peptide antigens obtained from blood using immunopurification of multiple histocompatability complexes, peptide elution and sample concentration, all as part of an integrated sample collection and introduction system for the mass spectrometer. The resultant mass displays can be compared with patient baseline displays to determine changes in patient immune response, to protein/genome databases, to broader patient population databases, and to known antigens. The mass spectrometer itself should be selected to provide sufficient mass resolution and mass accuracy to distinguish antigens, within the general mass range of about 700 to 1600 Daltons, in this example, as applied to class I peptide antigens. This provides a size, cost and ease of use that enables its widespread use within a clinical setting. While unit mass resolution would be a minimum requirement for assessing changes in display patterns, higher mass resolution to distinguishing isomass antigens with different composition and/or MS/MS analyses may also be used. In addition to initial diagnoses, the instrument and approach would be utilized in the assessment of disease progression and/or response to clinical therapies.

Although the case of class I peptide selection is described in particular detail, the invention is not limited to only this case. The case of class II peptide selection either alone or together with class I peptide selection may also be used. In that case, one would use a mass spectrometer that has sufficient mass resolution and mass accuracy over a suitable range, for example 500 to 2500 to cover both class I and class II ranges. Furthermore, this invention contemplates generally providing immunopurification in the sampling system (the "front end") to provide a set of peptides for mass spectral analysis.

Figure 3:
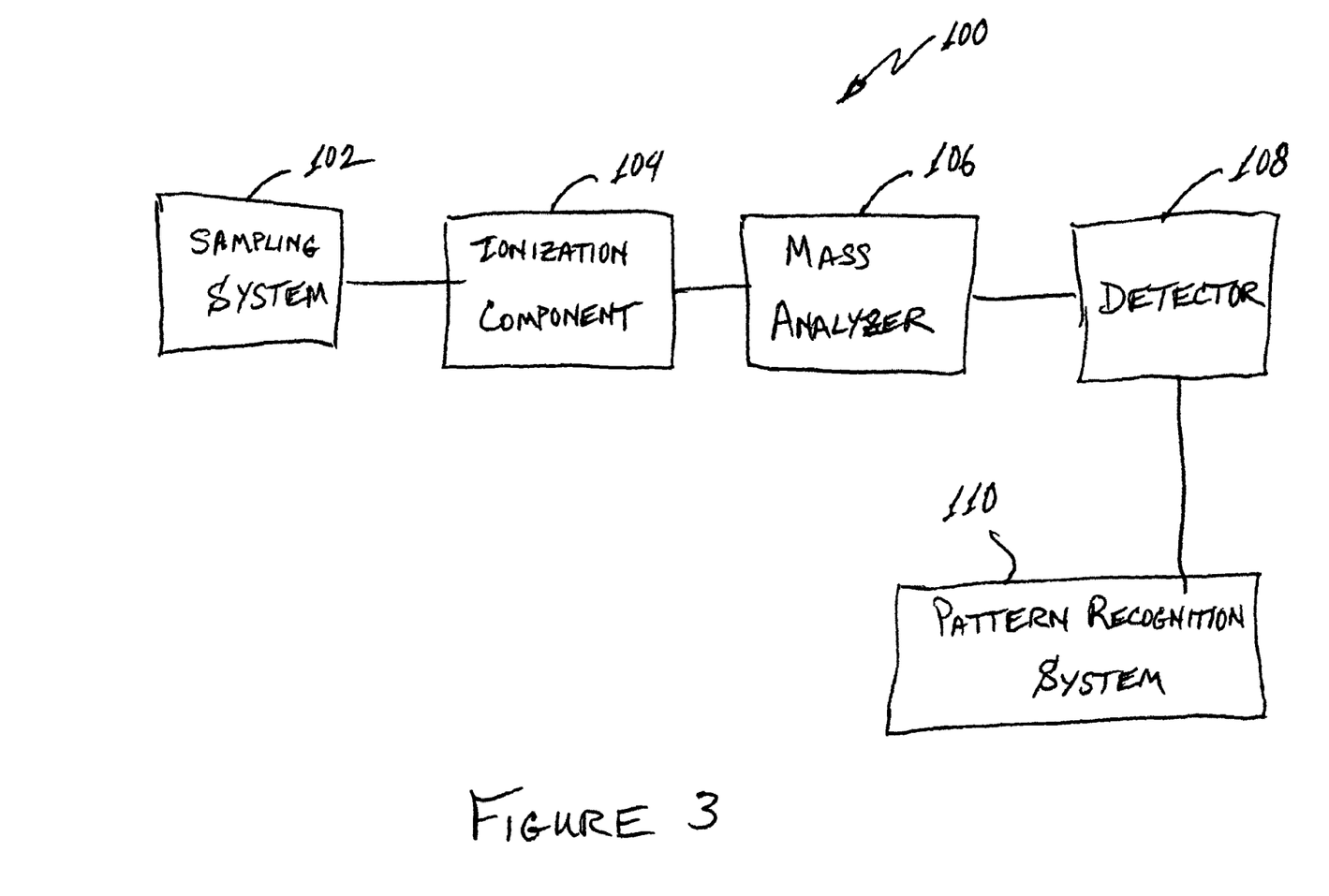
FIG. 3 is a schematic representation of a point-of-care mass spectrometer system according to an embodiment of this invention.

A point-of-care mass spectrometry system 100 according to an embodiment of the current invention is illustrated schematically in FIG. 3. The point-of-care mass spectrometer system 100 has a sampling system 102, an ionization component 104, a mass analyzer 106, a detector 108, and a pattern recognition system 110. The sampling system 102 processes a sample from a patient such as a sample of blood or other sample containing peptides to be selected for analysis. The sampling system provides immunopurification of MHC complexes, i.e., the capture of specific MHC complexes. The sampling system may also include equipment to wash the sample to remove unwanted proteins. This may then be followed by elution to obtain a subset of peptides from the original sample which then may be concentrated and loaded into the ionization component 104 of mass spectrometer (104, 106 and 108).

The ionization component 104 may be selected from ionization components suitable for the particular application. For example, MALDI and ESI have been found to be suitable ionization components. Ionized molecules from the sample are then introduced from an ionization component to the mass analyzer 106. The mass analyzer 106 may be selected from mass ionizers suitable for the particular application. A time-of-flight mass analyzer is suitable for many applications. For other applications, a quadrupole ion trap may also be suitable. A detector 108 then detects ionized molecules from the mass analyzer 106 to provide an output signal. The pattern recognition system 110 receives the signal output from the detector 108 to analyze the signal. The pattern recognition system 110 may be a special purpose hardwired system or may be a programmable system, such as a desktop or laptop computer programmed to perform a desired analysis. Similarly, the pattern recognition system 110 may include data storage and/or data reading components.

The point-of-care mass spectrometer system 100 is an embodiment which includes pattern recognition system 110. However, one may also have a point-of-care mass spectrometer system which does not include the pattern recognition system 110 in combination therewith. For example, one may collect data output from the detector 108 and analyze it separately from a point-of-care mass spectrometer system according to another embodiment of this invention.

A pattern recognition system 110 in an embodiment of the current invention analyzes the output from the detector 108 to determine a condition of a patient, or a change in condition of the patient. The pattern recognition system 110 may compare information from the output signal from the detector 108 to reference information which may be stored internally, stored on removable media, received from external storage components, or otherwise received. The output data from the detector 108 may be analyzed to produce a mass spectrum from the measured sample and may be compared to a reference mass spectrum. The reference mass spectrum may have been derived from data previously obtained from the same patient, it may be a mass spectrum containing known components, or it may be a mass spectrum obtained from a statistical analysis of data taken from several individuals.

In operation, a sample, such as a blood sample from a patient, is provided to the sampling system 102. The sampling system 102 provides immunopurification, for example, by the capture of MHC complexes. The sampling system 102 may then wash a sample to remove unwanted proteins, followed by elution to provide a subset of peptides from a blood sample to be concentrated and then loaded into the ionization component 104 of the point-of-care mass spectrometer system 100. Peptides from the sample that is ionized in the ionization component 104 are received by the mass analyzer 106. The detector 108 detects mass analyzed peptide ions to produce an output signal which is received by the pattern recognition system 110. The pattern recognition system 110 recognizes patterns in the signal from the detector 108, such as patterns in the mass spectrum measured from the sample. The pattern recognition system 110 may compare the signal output from detector 108 to a reference signal, which may be carried out by comparing a mass spectrum obtained from the signal from detector 108 to a reference mass spectrum. The reference signal, or reference mass spectrum, may be selected from references suitable to the specific task. For example, one may have a stored reference from the same patient, or even a history of previous reference signals or mass spectrums from the same patient. This can then be used to determine a change in a patient's condition from a previous time, for example, to detect the presence of infection and/or disease, or to monitor an effect of treatment. The reference data may also be obtained through a statistical analysis of data obtained from many individuals, and/or obtained through a mathematical model such as an empirical, semi-empirical or a theoretical model.

Figure 4:
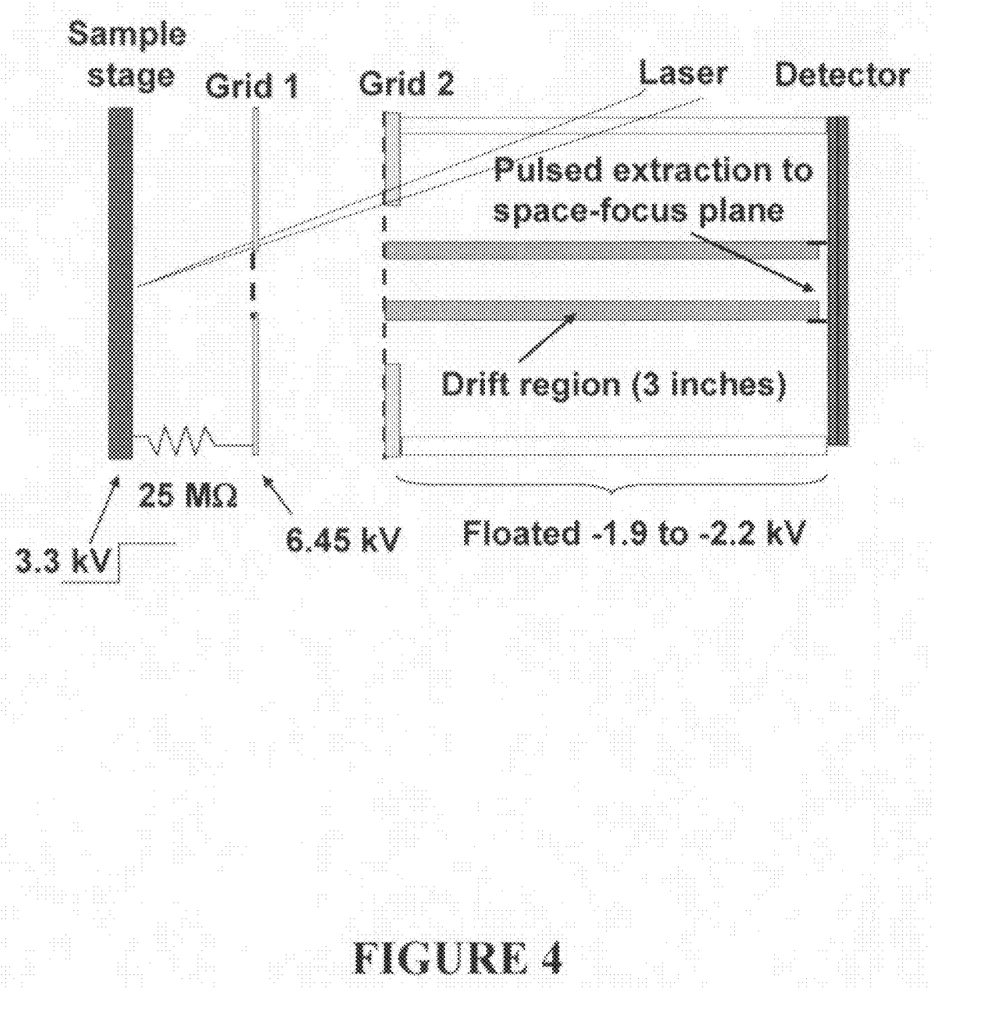
FIG. 4 is a schematic representation of a miniaturized pulse extraction time-of-flight mass spectrometer that is suitable for use in conjunction with a sample system and/or pattern recognition system according to the current invention.

In another embodiment, high order pulsed extraction focusing (FIG. 4) may be used to provide high mass resolution in a relatively compact time-of-flight mass spectrometer (see, Prieto, M. C.; Kovtoun, V. V. and Cotter, R. J., *Miniaturized Linear Time-of-Flight Mass Spectrometer with Pulsed Extraction*. J. Mass Spectrom. 37 (2002) 1158-1162; and Cotter, R. J.; English, R. D.; Warscheid, B.; Hardy, A.; and Gardner, B. D., *Miniaturized Time-of-Flight Mass Spectrometers for Bioagent Detection and Identification*, J. Mass Spectrom. Soc. Jpn. 51 (2003) 36-41, the entire contents of which are incorporated herein by reference).

High order kinetic energy focusing may also be achieved using non-linear reflectrons. (See, Cornish, T. J. and Cotter, R. J., *High Order Kinetic Energy Focusing in Endcap Reflectron Time-of-Flight Mass Spectrometer*. Anal. Chem. 69 (1997) 4615-4618; Cotter, R. J.; Fancher, C. and Cornish, T. J., *Miniaturized Time-of-Flight Mass Spectrometer for Peptide and Oligonucleotide Analysis*, J. Mass Spectrom. 34 (1999) 1368-1372; and Fancher, C. A.; Woods, A. S., and Cotter, R. J. *Improving the Sensitivity of the Endcap Reflectron Time-of-Flight Mass Spectrometer*, J. Am. Chem. Soc. 35 (2000) 157-162, the entire contents of which are incorporated herein by reference.)

Relatively compact mass spectrometers with higher mass resolution may also be achieved using orthogonal acceleration designs (Berkout, V. D.; Segers, D. P. and Cotter, R. J., *Miniaturized EI/Q/oa TOF Mass Spectrometer*, J. Am. Soc. Mass Spectrom. 12 (2001) 641-647, the entire contents of which are incorporated herein by reference). The display of peaks at nearly every mass within this mass range may make the distinction between signal and noise difficult. In that case, a tandem instrument incorporating a curved-field reflectron (Cotter, R. J.; Gardner, B.; Iltchenko, S. and English, R. D., *Tandem Time-of-Flight Mass Spectrometry with a Curved Field Reflectron*, Anal. Chem. 76 (2004) 1976-1981) can be used. Scanning of the mass selection gate in increments across the mass range will provide coherent product ion signal only when a precursor mass (and not noise) is encountered. This will improve signal to noise and in some cases distinguish antigens with the same mass.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

I claim:

1. A point-of-care mass spectrometer system, comprising:
a sampling system;
an ionization component structured to receive a sample for analysis from said sampling system;
a mass analyzer structured to receive a source of ions for analysis from said ionization component, and
a detector structured to detect ions from said mass analyzer and to generate an output signal,
wherein said sampling system selects a subset of peptides from a sample by immunopurification of multiple histocompatability complexes and concentrates said subset of peptides to provide said sample to said ionization component.

2. A point-of-care mass spectrometer system according to claim 1, further comprising a pattern recognition system which is in communication with said detector to receive said output signal from said detector,
wherein said pattern recognition system analyses said output signal from said detector to determine a condition or a change in condition of a patient.

3. A point-of-care mass spectrometer system according to claim 2, wherein said pattern recognition system compares information from said output signal from said detector to reference information to determine said condition or said change in condition of said patient.

4. A point-of-care mass spectrometer system according to claim 3, wherein said information from said output signal corresponds to a mass spectrum of said sample and said reference information corresponds to a reference mass spectrum.

5. A point-of-care mass spectrometer system according to claim 4, wherein said reference mass spectrum is a mass spectrum determined from a sample from said patient taken at a previous time.

6. A point-of-care mass spectrometer system according to claim 4, wherein said reference mass spectrum is a mass spectrum determined from a statistical analysis of mass spectra from a plurality of individuals.

7. A point-of-care mass spectrometer system according to claim 1, wherein said sampling system includes elution of said subset of peptides prior to concentrating said subset of peptides to provide said sample to said ionization component.

8. A point-of-care mass spectrometer system according to claim 1, wherein said mass analyzer is a time-of-flight mass analyzer.

9. A point-of-care mass spectrometer system according to claim 1, wherein said mass analyzer is a quadrupole ion trap mass analyzer.

10. A point-of-care mass spectrometer system according to claim 1, wherein said ionization component is a matrix-assisted laser desorption/ionization component.

11. A point-of-care mass spectrometer system according to claim 1, wherein said ionization component is an electrospray ionization component.

12. A point-of-care mass spectrometer system according to claim 1, wherein said mass analyzer has a sufficient mass resolution and mass accuracy in a range from about 500 to 2500 Daltons to distinguish antigens within the range.

13. A point-of-care mass spectrometer system according to claim 1, wherein said mass analyzer has a sufficient mass resolution and mass accuracy in a range from about 700 to 1600 Daltons to distinguish antigens within the range.

14. A clinical diagnostic method, comprising:
extracting a subset of peptides from a sample from a subject by immunopurification;
ionizing at least a portion of said subset of peptides to provide an ionized sample of peptides;
mass-analyzing said ionized sample of peptides to provide a mass analyzed sample of peptides;
detecting said mass analyzed sample of peptides to obtain a measured mass spectrum; and
recognizing a pattern in said measured mass spectrum to determine a condition or a change in condition of said subject.

15. A clinical diagnostic method according to claim 14, further comprising comparing said measured mass spectrum to a reference mass spectrum.

16. A clinical diagnostic method according to claim 15, wherein said reference mass spectrum is a mass spectrum previously obtained from the same subject.

17. A clinical diagnostic method according to claim 15, wherein said reference mass spectrum is a mass spectrum of currently known antigens.

18. A clinical diagnostic method according to claim 15, wherein said reference mass spectrum is a statistical mass spectrum obtained from a statistical analysis of a plurality of mass spectra.

19. A clinical diagnostic method according to claim 18, wherein said plurality of mass spectra were obtained from a plurality of individuals.

20. A clinical diagnostic method according to claim 14, wherein said immunopurification comprises capturing MHC-peptide complexes and eluting to obtain said subset of peptides.

21. A clinical diagnostic method according to claim 20, wherein said immunopurification further comprises washing away unwanted proteins from said sample after said capturing MHC-peptide complexes.

22. A clinical diagnostic method according to claim 20, wherein said MHC-peptide complexes are class I complexes.

23. A clinical diagnostic method according to claim 20, wherein said MHC-peptide complexes are class II complexes.

24. A clinical diagnostic method according to claim 14, wherein said ionizing includes electrospray ionization.

25. A clinical diagnostic method according to claim 14, wherein said ionizing includes matrix-assisted laser desorption/ionization.

26. A clinical diagnostic method according to claim 14, wherein said mass analyzing said ionized sample comprises time-of-flight mass analyzing.

27. A clinical diagnostic method according to claim 14, wherein said mass analyzing said ionized sample comprises mass analyzing with a quadrupole ion trap.

* * * * *